(12) United States Patent
Yamaya

(10) Patent No.: US 10,188,271 B2
(45) Date of Patent: Jan. 29, 2019

(54) ASSIST DEVICE AND ENDOSCOPE SYSTEM

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/616,025

(22) Filed: Jun. 7, 2017

(65) Prior Publication Data
US 2017/0265723 A1 Sep. 21, 2017

Related U.S. Application Data

(63) Continuation of application No. PCT/JP2015/080770, filed on Oct. 30, 2015.

(30) Foreign Application Priority Data

Dec. 10, 2014 (JP) .................................. 2014-250214

(51) Int. Cl.
*A61B 1/00* (2006.01)
*A61B 1/005* (2006.01)
(Continued)

(52) U.S. Cl.
CPC ............ *A61B 1/00133* (2013.01); *A61B 1/00* (2013.01); *A61B 1/0014* (2013.01);
(Continued)

(58) Field of Classification Search
CPC ............ A61B 1/00133; A61B 1/00071; A61B 1/00066; A61B 1/00128; A61B 1/018;
(Continued)

(56) References Cited

U.S. PATENT DOCUMENTS

2005/0065399 A1 3/2005 Sasaki et al.
2012/0203064 A1\* 8/2012 Wynberg ........... A61B 17/3421
600/106

FOREIGN PATENT DOCUMENTS

EP 1 987 794 A1 11/2008
EP 2 658 466 A1 11/2013
(Continued)

OTHER PUBLICATIONS

Translation of WO 2013065509, 13 pages.\*
(Continued)

*Primary Examiner* — Timothy J Neal
(74) *Attorney, Agent, or Firm* — Scully, Scott, Murphy & Presser P.C.

(57) ABSTRACT

An assist device which is applied to a treatment instrument including an insertion body to be inserted through a channel of an endoscope, and which is configured to assist movement of the insertion body relative to the channel, includes: a flexible tube including a passage into which the insertion body of the treatment instrument is inserted; a connector provided on the flexible tube and configured to connect to the endoscope to allow communication between the channel and the passage; a first retainer provided on the flexible tube and configured to hold an outer circumference of an insertion section of the endoscope or an outer circumference of an operation section connected to the insertion section; and a second retainer being movable relative to the first retainer and configured to hold the insertion body of the treatment instrument.

12 Claims, 8 Drawing Sheets

(51) Int. Cl.
*A61B 1/015* (2006.01)
*A61B 1/018* (2006.01)
*A61B 90/00* (2016.01)

(52) U.S. Cl.
CPC ........ *A61B 1/0052* (2013.01); *A61B 1/00119* (2013.01); *A61B 1/00128* (2013.01); *A61B 1/015* (2013.01); *A61B 1/018* (2013.01); *A61B 2090/3966* (2016.02)

(58) Field of Classification Search
CPC ....... A61B 1/06; A61B 1/00091; A61B 1/015; A61B 1/00112; A61B 1/0052; A61B 18/1482; A61B 1/0051; H04N 2005/2255; G02B 23/2461
See application file for complete search history.

(56) References Cited

FOREIGN PATENT DOCUMENTS

| JP | H07-059730 A | 3/1995 |
|---|---|---|
| JP | 2003-079564 A | 3/2003 |
| JP | 2005-058749 A | 3/2005 |
| JP | 2013-198673 A | 10/2013 |
| WO | WO 2013/065509 A1 | 5/2013 |

OTHER PUBLICATIONS

English translation of International Preliminary Report on Patentability dated Jun. 22, 2017 together with the Written Opinion received in related International Application No. PCT/JP2015/080770.

International Search Report dated Dec. 8, 2015 issued in PCT/JP2015/080770.

Japanese Office Action dated Nov. 29, 2016 issued in JP 2016-536272.

Extended Supplementary European Search Report dated Sep. 3, 2018 in European Patent Application No. 15 86 7725.2.

* cited by examiner

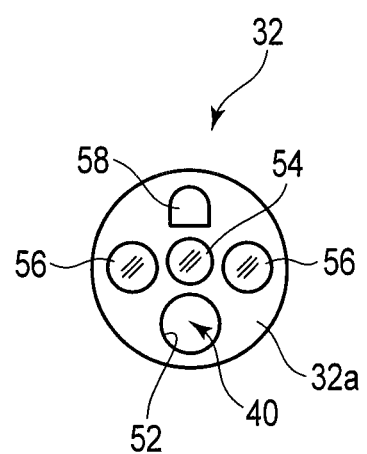
F I G. 2

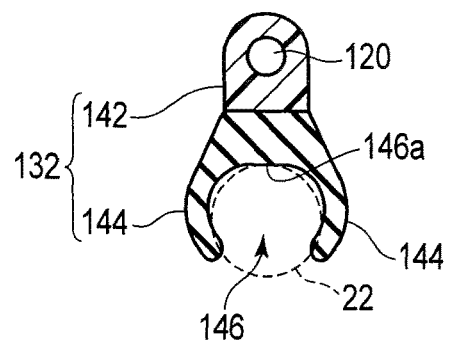
F I G. 5B
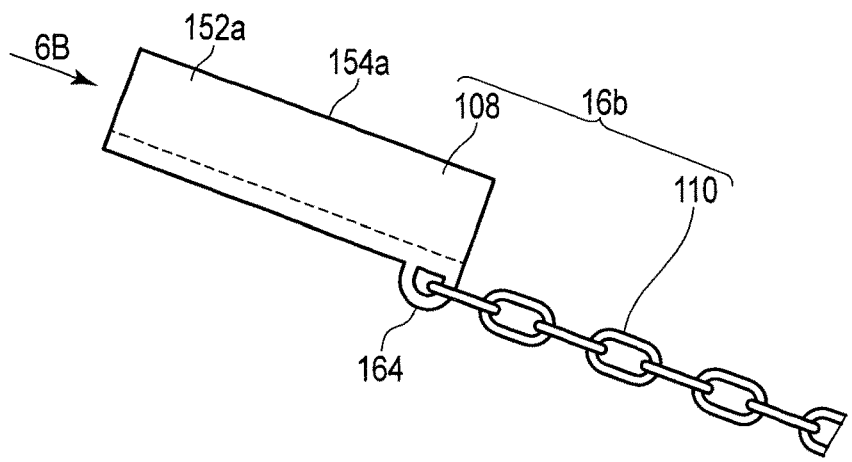
F I G. 6A
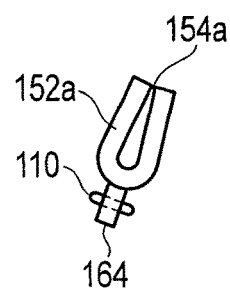
F I G. 6B

ASSIST DEVICE AND ENDOSCOPE SYSTEM

CROSS-REFERENCE TO RELATED APPLICATIONS

This application is a Continuation Application of PCT Application No. PCT/JP2015/080770, filed Oct. 30, 2015 and based upon and claiming the benefit of priority from prior Japanese Patent Application No. 2014-250214, filed Dec. 10, 2014, the entire contents of all of which are incorporated herein by reference.

BACKGROUND OF THE INVENTION

1. Field of the Invention

The present invention relates to an assist device which is attached to an endoscope to assist an operation of a treatment instrument, and also to an endoscope system including the assist device.

2 Description of the Related Art

A treatment instrument, which is configured to be inserted. through a channel of an endoscope, may be inserted into the channel or removed therefrom by a person other than the operator of the endoscope, an as to the operator. If the operator can operate the treatment instrument without the help of the assistant, this would enhance the efficiency. For example, International Publication No. 2013/065509 discloses an assist device including an operation member that enables the operator to insert a treatment instrument into a channel and remove the treatment instrument from the channel (namely, an advancing operation and a retreating operation) by himself or herself. A fixing member of this assist device is attached (fixed) to the outer circumference of the insertion section of the endoscope.

BRIEF SUMMARY OF THE INVENTION

According to an aspect of the invention, there is provided an assist device which is applied to a treatment instrument including an insertion body to be inserted through a channel of an endoscope, and which is configured to assist movement of the insertion body relative to the channel, includes: a flexible tube including a passage into which the insertion body of the treatment instrument is inserted; a connector provided on the flexible tube and configured to connect to the endoscope to allow communication between the channel and the passage; a first retainer provided on the flexible tube and configured to hold an outer circumference of an insertion section of the endoscope or an outer circumference of an operation section connected to the insertion section; and a second retainer being movable relative to the first retainer and configured to hold the insertion body of the treatment instrument.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a schematic view illustrating how the distal face of the distal structural portion of an insertion section is in the endoscope system of the first embodiment.

FIG. 5B is a cross sectional view taken along line 5B-5B shown in FIG. 5A.

FIG. 6A is a schematic diagram illustrating the accessory to the assist device of the endoscope system according to the modification of the first embodiment.

FIG. 6B is a schematic diagram illustrating how the second retainer of the accessory shown in FIG. 6A looks like when it is viewed in the direction indicated by arrow 6B.

DETAILED DESCRIPTION OF THE INVENTION

Figure 1:
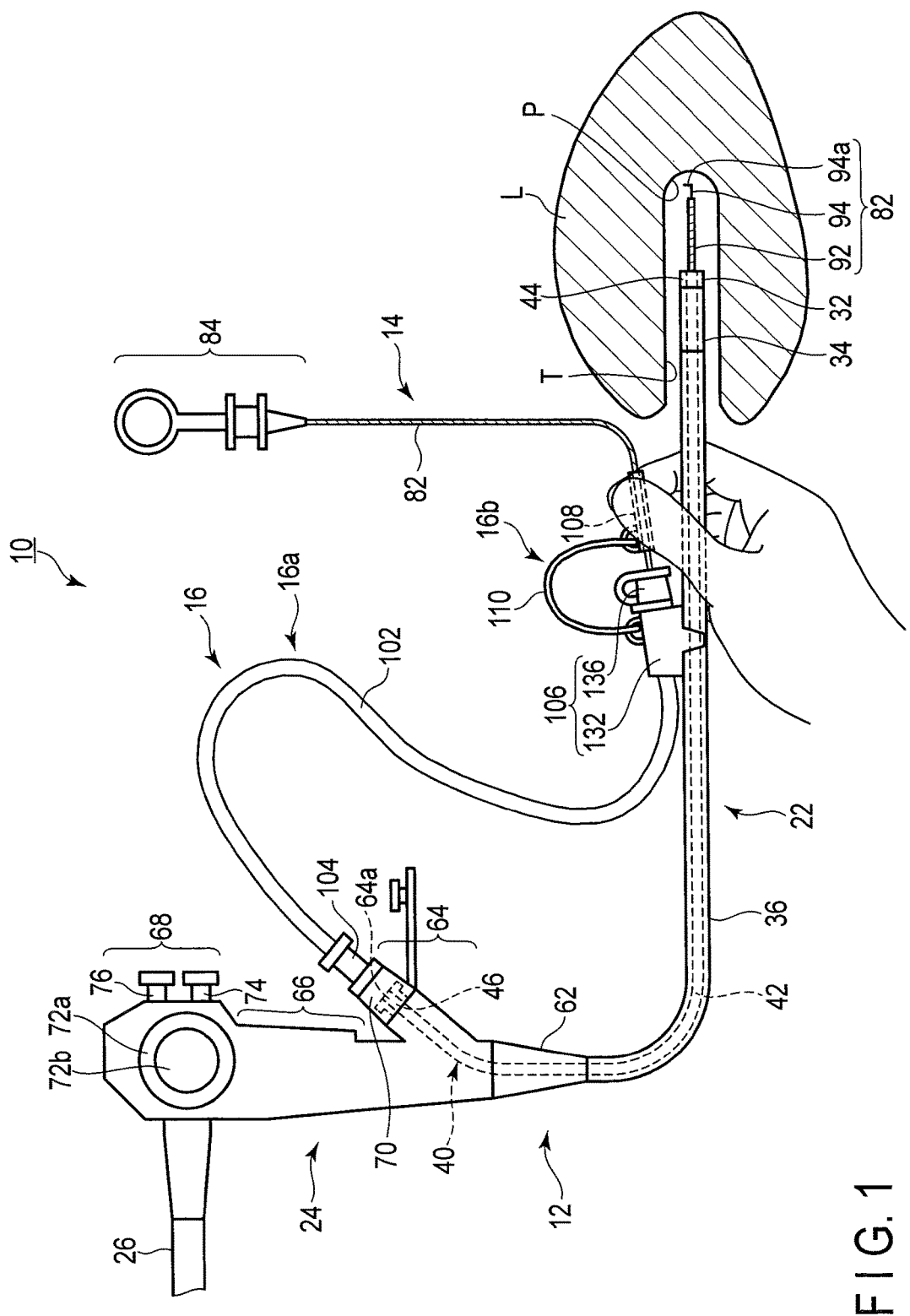
FIG. 1 is a schematic diagram showing an endoscope system according to the first embodiment and illustrating a state where a treatment instrument is inserted into an assist device or the channel of an endoscope, with the assist device attached to the endoscope.

Hereinafter, embodiments of the present invention will be described with reference to the accompanying drawings.

The first embodiment will be described with reference to FIGS. 1 to 4.

The endoscope system (endoscope apparatus) 10 of the present embodiment includes an endoscope 12, a treatment instrument 14 and an assist device 16. The treatment instrument 14 is movable relative to the treatment instrument insertion channel 40 (described later) of the endoscope 12. One end (the distal end) of the assist device 16, which is located close to the distal end of the insertion section 22 of the endoscope 12, is detachably fixed to the insertion section 22 of the endoscope 12 or to an operation section 24 thereof, while the other end (the proximal end) of the assist device 16 is detachably held by the operation section 24 of the endoscope 12. The assist device 16 is used as an aid in the movements (advancing/retreating movement and rotation) of the treatment instrument 14 relative to the channel 40. The treatment instrument 14 includes an insertion body 82

(described later), which is inserted into the channel 40 of the endoscope 12 by the operator. The assist device 16 assists the movement of the treatment instrument 14 (which is extended from one end of the assist device 16 by the operator) relative to the endoscope 12.

In the description below, reference will be made to the case where the outer circumference of the insertion section 22 is held by the distal end of the assist device 16. Where the operation section 24 is held by the distal end of the assist device 16, it is preferred that a bending preventing section 62 be held. The case where the operation section 24 is held by the distal end of the assist device 16 is, for example, a case where the insertion section 22 is short.

The structure of the endoscope 12 will be briefly described with reference to FIG. 1. The endoscope 12 may be a known type including a channel 40 (described below). As shown in FIG. 1, the endoscope 12 includes a thin, elongated insertion section 22, an operation section 24 continuous with the proximal portion of the insertion section 22, and a universal cord 26 extending from a side portion of the operation section 24.

The insertion section 22 includes, from the distal end to the proximal end, a hard distal structural portion 32, a bendable section 34 which is made bendable by bending pieces (not shown) arranged in series, and a flexible tube 36 which is flexibly bendable when exerted with an external force.

A channel tube (treatment instrument insertion channel tube) 42, which forms a treatment instrument insertion channel 40, is provided inside the insertion section 22. The distal end 44 of the channel tube 42 is connected to the distal side opening 52 (described later) through the distal structural portion 32. Preferably, the treatment instrument insertion channel 40 has branches portions inside the operation section 24, as is known in the art. The first proximal end 46 of the treatment instrument insertion channel 40 is connected to a proximal side opening (a plug connection sleeve) 64a, which will be described later. The second proximal end (not shown) of the treatment instrument insertion channel 40 is connected to a suction button 76 (described later) of a suction mechanism. Of the portions of the treatment instrument insertion channel 40, that portion located between the distal side opening 52 of the distal structural portion 32 and the branch position of the treatment instrument insertion channel 40 is formed as an insertion passage through which the insertion body 82 of the treatment instrument 14 is inserted. That portion also function s as a suction tube. It should be noted that the endoscope 12 of the present embodiment does not have to employ a suction mechanism.

As shown in FIG. 2, the distal structural portion 32 includes, on the distal surface 32a thereof, the distal side opening 52, an observation window 54, one or two illumination windows 56 (two illumination windows are desirable) and a nozzle 58. As shown in FIG. 1, the distal side opening 52 communicates with the distal end of the channel tube 42 and forms a distal end portion of the treatment instrument insertion channel 40. The observation window 54 forms a distal end portion of an observation optical system, through which an observation target is observed. The illumination windows 56 form a distal end portion of an illumination optical system, by which the observation target is illuminated. The nozzle 58 discharges a gas or a liquid from a discharge port (not shown) provided in the observation window 54. The gas and the liquid are discharged in response to an operation of an air/water button 74 (described. later).

As shown in FIG. 1, the operation section 24 includes, from the distal side to the proximal side, the bending preventing section 62, a treatment instrument inlet port 64, a grip section 66 and an operation section main body 68. Preferably, the treatment instrument inlet port 64, the grip section 66 and the operation section main body 68 are integrally formed as one body. The bending preventing section 62 holds the proximal end portion of the flexible tube 36 and restrains the proximal end portion of the flexible tube 36 of the insertion section 22 from being bent.

The treatment instrument inlet port 64 is provided with a proximal side opening (plug connection sleeve) 64a, to which the first proximal end 46 of the channel tube 42 is connected. An assist device valve 70 is attached to the proximal side opening 64a of the treatment instrument inlet port 64. In the state where the insertion body 82 (described later) of the treatment instrument 14 and a connector 104 (described later) of the assist device 16 are inserted, the assist device valve 70 has a valve structure which prevents a liquid flowing through the channel tube 42 toward the proximal side from leaking to the outside of the endoscope 12. The assist device valve 70 may be similar to a known forceps valve.

The grip section 66 is a section gripped by a hand (e.g., the left hand) of the operator. The operation section main body 68 is operated to bend the bendable section 34. The universal cord 26 extends from a side portion of the operation section main body 68.

The operation section main body 68 is provided with bending operation knobs 72a and 72b, the air/water button 74 and the suction button. 76. The bending operation knobs 72a and 72b enable remote control of the bending operation of the bendable section 34. Typically, the operator holds the grip section 66 with the palm of the left hand, and operates the bending operation knobs 72a and 72b with the thumb or a finger of the left hand. Since an air/water supply mechanism including the air/water button and a suction mechanism including the suction button 76 are known in the art, a description of these mechanisms will be omitted herein.

The treatment instrument 14 includes an insertion body 82 that can be inserted into the channel 40 of the endoscope 12, and a base (operation portion) 84 that is located at the proximal end of the insertion body 82. The insertion body 82 is longer than the overall length of the channel 40. For example, the insertion body 82 may be several times longer than the channel 40. The distal end of the insertion body 82 can be inserted through the channel 40 of the endoscope 12 and moved in or out with reference to the distal structural portion 32 of the insertion section 22.

The insertion body 82 includes a sheath 92, and a wire 94 having an end effector 94a at the distal end thereof. The sheath 92 may be a resin tube having insulation property or a coil sheath, either of which is selectable in accordance with the type of end effector 94a. The wire 94 is flexible.

The end effector 94a may be substantially L-shaped, in the form of a snare, in the form of a basket, or the like. The end effector 94a can perform proper treatment using high-frequency energy with respect to a living tissue in front of a return electrode (not shown) attached to the patient.

The base 84 includes a known type of slider mechanism. By operating the slider mechanism of the base 84, the wire 94 is axially movable relative to the sheath 92. Therefore, the slider mechanism enables the wire 94 to be moved back and forth in the axial direction of the insertion body 82 relative to the sheath 92. Where the sheath 92 and wire 94 of the insertion body 82 are held by the operator, they can be rotated together around the axis of the insertion body 82.

A description will now be given, with reference to FIGS. 1 and 3A-3C, of the assist device 16 to advance or retreat the treatment instrument 14 relative to the channel 40 of the endoscope 12.

The assist device 16 includes an assist device main body 16a and an accessory 16b.

The assist device main body 16a includes an elongated flexible tube 102, a connector 104 which is detachably couples the proximal side (connection end) of the flexible tube 102 to the proximal side opening 64a, and a first retainer 106 which retains the outer side of the insertion section 22 of the endoscope 12 on the distal side (moving end) of the flexible tube 102. The accessory 16b is attached to the insertion body 82 in such a manner as to retain the insertion body 82 of the treatment instrument 14. The accessory 16b includes a second retainer 108 held by the operator and a connecting member 110 which connects the first retainer 106 and the second retainer 108 together. The first retainer 106 and the second retainer 108 are separate from each other during use. The second retainer 108 is attachable to, or detachable from the first retainer 106.

Preferably, the flexible tube 102 is a tube which is easy to bend, is hard to wind, and ensures smooth sliding movement of the insertion body 82 of the treatment instrument 14. For example, the flexible tube 102 may be a fluoroplastic tube, a fluoroplastic tube containing a blade to improve the bending strength, or a blade-contained polyurethane resin. tube having a fluoroplastic coating on the passage 120 inside the flexible tube 102 so that the insertion body 82 of the treatment instrument 14 can be easily advanced or retreated in the axial direction, or the like. The overall length of the flexible tube 102 is less than the overall length of the insertion body 82 of the treatment instrument 14 but should be 500 mm or more.

Figure 3A:
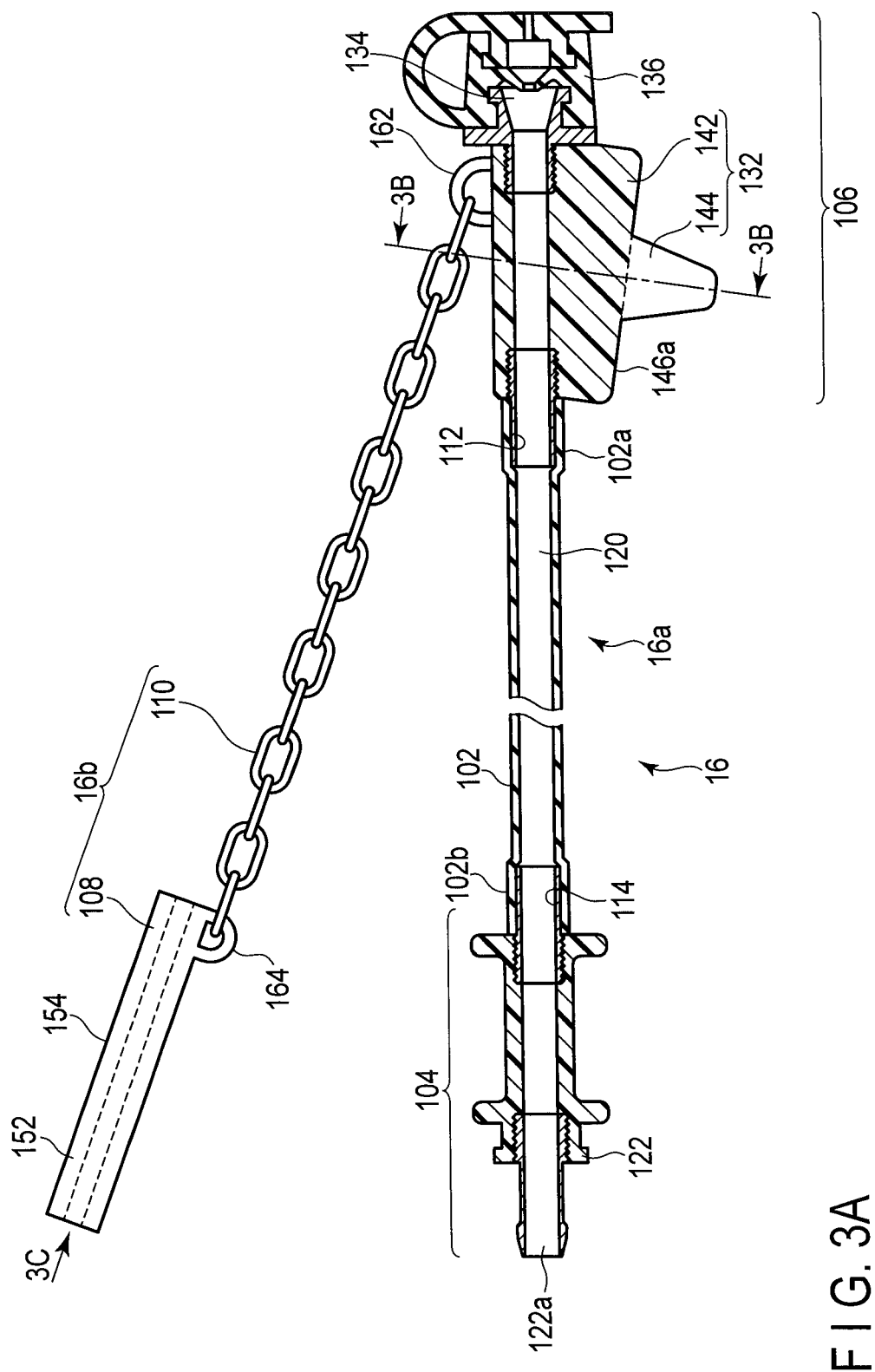
FIG. 3A shows the assist device of the endoscope system of the first embodiment, the main body of the assist device being depicted as a longitudinal sectional view, and an accessory depicted as a schematic diagram.

The flexible tube 102 includes pipe sleeves 112 and 114 at the distal end 102a and proximal end 102b, respectively. The distal side pipe sleeve 112 is connected to the first retainer 106. The proximal side pipe sleeve 114 is connected to the connector 104. In FIG. 3A, the distal end 102a of the flexible tube 102 is shown being in contact with the first retainer 106. In place of this structure, the distal end 102a of the flexible tube 102 may be separate from the distal side pipe sleeve 112. For this reason, the first retainer 106 may be attached in the neighborhood of the distal end of the flexible tube 102. In FIG. 3A, the proximal end 102b of the flexible tube 102 is shown being in contact with the connector 104. In place of this structure, the proximal end 102b of the flexible tube 102 may be separate from the proximal side pipe sleeve 114. For this reason, the connector 104 may be attached in the neighborhood of the proximal end of the flexible tube 102.

The flexible tube 102, the connector 104 and the first retainer 106 of the assist device 16 form the passage 120. The passage 120 is formed throughout the overall length of the assist device 16, and the insertion body 82 of the treatment instrument 14 is inserted into the passage 120.

The connector 104 includes a connecting pipe sleeve 122 having a proximal side opening end 122a of the passage 120. The connecting pipe sleeve 122 is coupled to the assist device valve 70 such that the valve structure of the assist device valve 70 is opened at the proximal side opening end 122a. To be more specific, in the present embodiment, the connecting pipe sleeve 122 of the connector 104 is inserted and fitted in a depressed section (now shown) of the assist device valve 70 formed of an elastic material and attached to the proximal side opening 64a of the endoscope 12. With this structure, the connector 104 of the assist device 16 communicates with the treatment instrument insertion channel 40 of the endoscope 12 by way of the assist device valve 70 of the proximal side opening (a plug connection sleeve) 64a of the endoscope 12, and therefore permits communication between the channel 40 and the passage 120. The connector 104 of the assist device 16 is attachable to or detachable from the assist device valve 70 attached to the proximal side opening (plug connection sleeve) 64a of the endoscope 12.

The first retainer 106 includes a main body 132, a connecting pipe sleeve 134 attached to the main body 132, and a treatment instrument valve 136. The connecting pipe sleeve 134, which is similar to the proximal side opening (plug connection sleeve) 64a of the endoscope 12, is fixed to the main body 132. Like the assist device valve 70 mentioned above, the treatment instrument valve 136 may be similar to a known forceps valve. With the valve structure of the treatment instrument valve 136, a body fluid in the body cavity flowing backward through the treatment instrument insertion channel 40 of the endoscope 12 and the passage 120 of the assist device 16 is prevented from leaking to the outside. The treatment instrument valve 136 through which the insertion body 82 of the treatment instrument 14 is inserted serves to prevent a liquid (such as a body fluid flowing through the treatment instrument insertion channel 40 of the endoscope 12 and the passage 120 of the assist device 16) from leaking to the outside.

The main body 132 of the first retainer 106 is formed of synthetic resin, for example. The main body 132 of the first retainer 106 includes a base 142 forming the proximal end portion of the passage 120, and a pair of arms 144 projected from the base 142. A cutout 146 is formed between the arms 144. When the main body 132 of the first retainer 106 is attached to or detached from the outer circumferential surface of the insertion section 22 indicated by the broken line, the arms 144 are elastically deformed, and the cutout 146 are temporarily expanded. Thus, the attachment and detachment of the main body 132 are easy. The first retainer 106 can detachably hold the outer circumferential surface of the insertion section 22 by means of the base 142 (a contact surface 146a described later) and the arms 144.

The main body 132 of the first retainer 106 is detachably attached to the outer circumferential surface of the insertion section 22, as described above. Desirably, the main body 132 is fixed to the outer circumferential surface, with a proper fixing force applied. The fixing force with which to fix the main body 132 of the first retainer 106 to the outer circumferential surface of the insertion section 22 is determined such that in the state where the outer circumferential surface of the insertion section 22 is held with the ring and little fingers of the right hand, the arms 144 of the first retainer 106 can be properly moved along the axis of the insertion section 22 or around that axis with the thumb and index finger of the right hand. That is, the position of the first retainer 106 can be properly adjusted, with the insertion section 22 of the endoscope 12 being held with the right hand. of the operator. As described above, the first retainer 106 is not immovable relative to the outer circumference of the insertion section 22 of the endoscope 12. In the state where the outer circumferential surface of the insertion section 22 is held with the right hand, the operator can move the main body 132 of the first retainer 106 to a position where it can be easily operated with the right hand.

Figure 4:
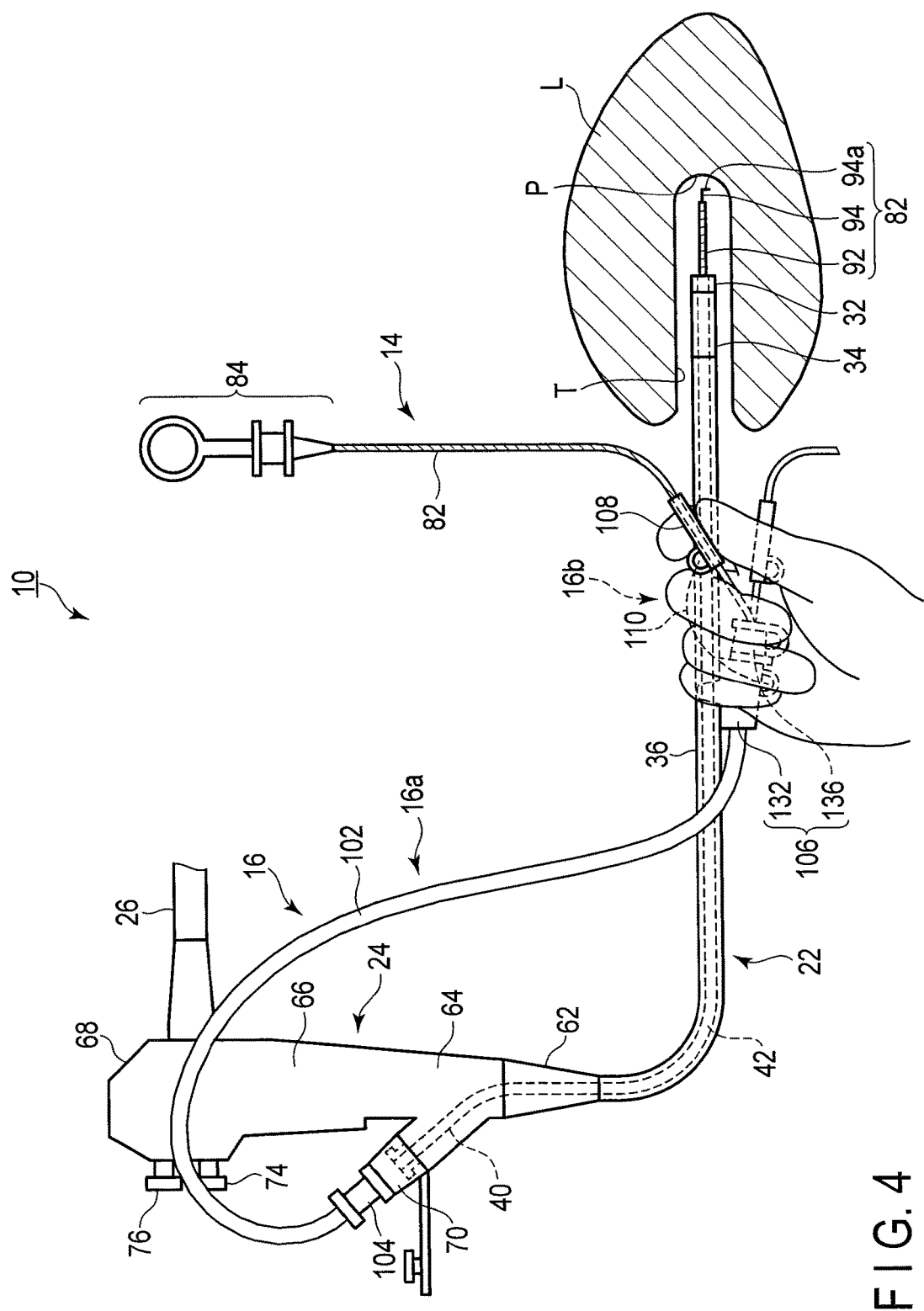
FIG. 4 is a schematic diagram showing the endoscope system of the first embodiment, and illustrates a state where the treatment instrument is inserted into the assist device and the channel of the endoscope, with the assist device attached to the endoscope, as well as a state where the insertion section is rotated 180° around its axis.

Desirably, the base 142 has a contact surface 146a inclined. with reference to the longitudinal axis of the passage 120 of the base 142 and located between the pair of arms 144. The contact surface 146a of the base 142 can detachably hold the outer circumferential surface of the insertion section 22 in cooperation with the arms 144. When the first retainer 106 is attached to the outer circumferential surface of the insertion section 22 of the endoscope 12, the contact surface 146a of the base 142 moves the treatment instrument valve 136 away from the insertion section 22 of the endoscope 12 and moves the distal side pipe sleeve 112 and the distal end 102a of the flexible tube 102 closer to the insertion section 22 of the endoscope 12. As shown in FIGS. 1 and 4, therefore, the distal end 102a of the flexible tube 102 can be moved closer to the insertion section 22 of the endoscope 12. Unlike the case where the distal end 102a of the flexible tube 102 is located away from the insertion section 22, the flexible tube 102 does not become an obstacle when the insertion section 22 and the second retainer 108 are operated.

The second retainer 108 is separate from the first retainer 106 and is movable. The second retainer 108 includes an elastically-deformable tubular retainer body 152 having an inner diameter smaller than the outer diameter of the insertion body 82 of the treatment instrument 14 and an outer diameter larger than the outer diameter of the insertion body 82 of the treatment instrument 14. A slit 154 allowing communication between the inside and the outside is formed in the retainer body 152. The length of the retainer body 152 is determined such that the retainer body 152 can be easily operated in the state where it is pinched with the thumb and the index finger. Preferably, the length of the retainer body 152 is in the range of 10 mm to 50 mm. Preferably, the outer diameter of the retainer body 152 is in the range of 5 mm to 10 mm.

The slit 154 is formed along the longitudinal axis of the retainer body 152 and extends throughout the overall length from one end to the other of the retainer body. With this structure, the insertion body 82 of the treatment instrument 14 can be inserted into the assist device main body 16a of the assist device 16, and subsequently the second retainer 108 can be moved away from the insertion body 82. That is, the second retainer 108 can be easily attached or detached laterally.

Desirably, the slit 154 has a width substantially equal to the outer diameter of the insertion body 82 or slightly less than that outer diameter. In FIG. 3C, the slit 154 is shown as being linear, but it may be curved, including a wavelike shape or a spiral shape.

The second retainer 108 is formed of a material which does riot slide on the outer circumferential surface of the insertion body 82 of the treatment instrument 14 and which can therefore hold the outer circumferential surface by friction. The second retainer 108 is formed of an elastic material, such as silicone rubber. The material of the second retainer 108 is not limited to silicone rubber but may be any kind of material, provided that it can be easily deformed when the second retainer 108 is attached to or detached from the outer circumferential surface of the insertion body 82 of the treatment instrument 14 and that the insertion body 82 can be held without sliding after the second retainer 108 is attached.

The main body 132 of the first retainer 106 is provided with a first supporting section 162 which supports the proximal end of the connecting member 110. The first supporting section 162 is formed on the base 142. The first supporting section 162 may be integrally formed with the base 142, using a plastic material; alternatively, it may be formed of a metallic material. The retainer body 152 of the second retainer 108 is provided. with a second supporting section 164 which supports the proximal end of the connecting member 110. The first and second supporting sections 162 and 164 are formed in the form of a ring, for example. The second supporting section 164 may be integrally formed with the retainer body 152 of the second retainer 108. For example, the second supporting section 164 may be formed of a metallic material. Owing to this, the second retainer 108 is formed in such a manner as to include an elastic member (retainer body 152).

The connecting member 110 is, for example, a chain, a cord member, a flexible or stretchable rubber member, a vinyl tie, or the like. Therefore, the second retainer 108 can be moved relative to the first retainer 106 within the range determined by the length of the connecting member 110. Desirably, the overall length of the connecting member 110 is 100 mm or so.

Where the connecting member 110 is a chain, it is formed of a plastic material, for example. The connecting member 110 is not, limited to any particular material, shape or length, provided that the insertion body 82 of the treatment instrument 14, which is pinched by the operator by means of the second retainer 108, can be freely advanced or retreated relative to the first retainer 106.

In FIG. 3A, the other end of the connecting member 110 is shown being supported by the main body 132 of the first retainer 106, but this is not restrictive. For example, the other end of the connecting member 110 may be supported by the treatment instrument valve 136. The connecting member 110 need not be supported at any particular position. For example, the other end of the connecting member 110 may be coupled to an annular member (not shown) which is freely movable along the outer circumference of the flexible tube 102 of the assist device main body 16a.

The method for connecting the proximal side opening end 122a of the connector 104 and the proximal side opening 64a of the endoscope to each other is not limited to the method described above with reference to FIG. 1. For example, the connector 104 may be fixed directly to the proximal side opening 64a without using the assist device valve 70. Any method may be used as long as the connection ensures a liquid tight structure and the connector 104 is detachable. For example, the connector 104 may be formed of an elastic material, such as silicone rubber, instead of a resin material. In this case, the connector 104 can be fitted and fixed to the end of the proximal side opening 64a of the endoscope 12 in a liquid-tight manner. Furthermore, the connector 104 of the assist device main body 16a may be omitted. In this case, the proximal side pipe sleeve 114 at the proximal end 102b of the flexible tube 102 is inserted into the treatment instrument insertion channel 40 by way of the assist device valve 70. With this structure, the proximal end of the assist device 16 can be fixed to the endoscope 12.

How the endoscope system 10 having the above-mentioned structure operates will be described with reference to FIGS. 1 and 4. First, a brief description will be given of an endoscopic submucosal dissection (ESD), in which the submucosa of a disease portion P is filled with such a liquid as a physiological salt solution and the periphery of the disease portion P is dissected using a cautery knife.

The operator grips the grip section 66 of the operation section 24 of the endoscope 12 with the left hand, and holds the outer circumferential surface of the insertion section 22 with the right hand. Watching the observation image which the observation optical system of the endoscope 12 displays on a monitor (not shown), the operator gradually inserts the distal structural portion 32 at the distal end of the insertion section 22 toward the disease portion P by way of a hole of a lumen (body cavity) T, which is a passage (hole) of a living tissue L. While gripping the grip section 66 of the operation section 24 of the endoscope 12 with the left hand, the operator properly operates the bending operation knobs 72a and 72b with the left hand and advances, retreats or twists the insertion section 22 with the right hand. The operator continues to insert the distal structural portion 32 of the insertion section 22 until the distal structural portion 32 comes to a position away from the disease portion P by a proper distance. In the state where the operator holds the insertion section. 22 of the endoscope 12 with the right hand and the positional relation between the distal surface 32a of the distal structural portion 32 of the insertion section 22 and the disease portion P is maintained, an assistant (another operator) attaches the connector 104 provided at, the proximal end of the assist device 16 to the proximal side opening (plug connection sleeve) 64a of the endoscope 12. Subsequently, the assistant inserts the insertion body 82 of the treatment instrument 14 into the passage 120 of the assist device main body 16a and the channel 40 of the endoscope 12 until the end effector 94a is arranged in the neighborhood of the distal structural portion 32 of the insertion section 22 of the endoscope 12. Then, the assistant arranges the first retainer 106 of the assist device main body 16a on the outer circumferential surface of the insertion section 22 of the endoscope 12, and arranges the second retainer 108 of the axial accessory 16b on the outer circumferential surface of the insertion body 82 of the treatment instrument 14 in a lateral direction of the insertion body 82.

While maintaining the direction and position of the distal structural portion 32 of the insertion section 22 of the endoscope 12, the operator moves the right hand and holds the first retainer 106 with the palm, the middle, ring and little fingers of the right hand. Simultaneously, the operator holds the second retainer 108 with the thumb and the index finger of the right hand. The middle finger of the right hand may hold either the first retainer 106 or the second retainer 108.

Preferably, the assistant should attach the assist device main body 16a to the endoscope 12 after the distal structural portion 32 of the insertion section of the endoscope 12 comes close to the disease portion P and an insertion position of the disease portion P is determined. This is for reducing the moving range of the retainer body 152 of the second retainer 108 held with the thumb and the index finger in the state where the first retainer 106 and the insertion section 22 of the endoscope 12 are held by the operator. The maximal moving range of the retainer body 152 changes depending upon the size of the right hand of the operator, the flexibility of the joints, and the like. The range in which the second retainer 108 can be moved. closer to or away from the first retainer 106 is, for example, several centimeters.

In the assist device 16 applied to forward or backward movement of the treatment instrument 14, the connector 104 located at the proximal end of the assist device 16 is connected to the proximal side opening 64a of the endoscope 12 by means of the assist device valve 70. The first retainer 106 at the distal end of the assist device 16 is detachably attached to the insertion section 22 of the endoscope 12 by means of a pair of arms 144. The position where the first retainer 106 at the distal end of the assist device 16 is attached to the insertion section 22 changes, depending upon how deep the disease portion. P is located from the hole of the lumen T. While holding the insertion section 22 of the endoscope 12 with the right hand, the operator can properly reattach the first retainer 106 to an optimal position on the insertion section 22.

By fitting the proximal end of the assist device main body 16a with the endoscope 12, an insertion port (the treatment instrument valve 136) to be inserted into the channel 40 by way of the assist device main body 16a can be moved from the proximal side opening (plug connection sleeve) 64a of the operation section 24 to a position close to the outer circumferential surface of the insertion section 22. Although the treatment instrument valve 136 is located at a position close to the outer circumferential surface of the insertion section 22, it has to be operated by the operator, with the insertion body 82 of the treatment instrument 14 being inserted into the passage 120 by the assistant. Therefore, the treatment instrument valve 136 is moved away from the outer circumferential surface of the insertion section 22 by the contact surface 146a, thereby permitting the assistant to easily insert the end effector 94a at the distal end of the insertion body 82 into the passage 120.

A more specific description will be given of how the operation uses the right hand. The insertion section 22 and the distal end portion of the assist device 16 are held with the palm, the middle, ring and little fingers, while simultaneously the insertion body 82 of the treatment instrument 14 or the retainer body 152 of the second retainer 108 detachably fixed to the insertion body 82 of the treatment instrument 14 is pinched with the thumb and the index finger. By moving the second retainer 108 of the assist device 16 in the axial direction without the right hand losing hold of the insertion section 22, the insertion body 82 of the treatment instrument 14 can be advanced or retreated by means of the second retainer 108 (namely, the first and second retainers 106 and 108 can be moved closer to each other or away from each other). That is, the insertion body 82 can be moved, for exam, 10 mm or so in the axial direction, for fine adjustment. While holding the insertion section 22 with the right hand, the operator can slightly change, using the same right hand, a projection length of the end effector 94a of the treatment instrument 14, namely, how the end effector 94a is projected from the distal structural portion 32 of the insertion section 22 of the endoscope 12. With the projection length being adjusted, the operator can make a high-frequency incision with the treatment instrument using high-frequency energy.

Typically, the base 84 of the treatment instrument 14 is operated by an assistant (not the operator) under the instructions of the operator. Typically, the output of high-frequency energy is started or stopped in response to the foot switch being operated by the operator.

While holding the insertion section 22 with the palm and the middle, ring and little fingers of the right hand, the operator pinches the second retainer 108 with the thumb and the index finger, and rotates the second retainer 108 on its own axis. As a result, the insertion body 82 inside the second retainer 108 can be moved relative to the channel 40. That is, the direction of the end effector 94a can be adjusted without changing the position and direction of the distal structural portion 32 of the insertion section 22 of the endoscope 12.

Since the insertion body 82 of the treatment instrument 14 has to be inserted into the channel 40, it is very thin and hard for the operator to pinch. The assist device 16 of the present embodiment has an increased grip (pinch) area and is easy to grip because the second retainer 108 is attached to the insertion body 82 of the treatment instrument 14, with the slit 154 (FIGS. 3A and 3C) of the retainer body 152 being elastically deformed and widened. As a result, the operator can easily operate (advance, retreat or rotate) the insertion body 82 of the treatment instrument 14 by means of the second retainer 108, while simultaneously holding the insertion section 22.

Depending upon the position of the disease portion P, there may be case where the distal surface 32a of the distal structural portion 32 cannot obtain a front view of the disease portion P unless the insertion section 22 is largely twisted around its axis. If the operator twists the insertion section 22, the insertion body 82 of the assist device 16 is moved in accordance therewith, as shown in FIG. 4. Accordingly, the distal end of the insertion body 82 of the assist device 16 moves in accordance with the twisting motion of the insertion section 22. Even if the insertion section 22 is rotated 180° from the state shown in FIG. 1 to the state shown in FIG. 4, the second retainer 108 is movable because it is connected to the first retainer 106 by means of the connecting member 110. Accordingly, the second retainer 108 can be moved to a position where it can be easily held with the thumb and the index finger, without reference to whether or not the insertion section 22 is twisted or how the insertion section 22 is twisted. The operator can therefore operate (advance, retreat or rotate) the treatment instrument 14, even if the insertion section 22 is twisted from the state shown in FIG. 1 to the state shown in FIG. 4.

In an ESD treatment, a plurality of treatment instruments 14 are replaced to the assist device main body 16a and the channel 40 of the endoscope 12 several times. Replacement of one treatment instrument 14 with another is performed not by the operator who holds the insertion section 22 of the endoscope 12 but by an assistant (i.e., another operator).

First of all, a first treatment instrument (a marking treatment instrument) is used to mark the periphery of a disease portion P. Then, the first treatment instrument is replaced with a second treatment instrument (a local injection treatment instrument), and a medical agent (such as a physiological salt solution) is locally injected to the submucosa of the disease portion P. Thereafter, the second treatment instrument is replaced with a third treatment instrument (e.g., a high-frequency knife), and the mucous membrane around the disease portion P is dissected in such a manner as to surround the marking by use of the third treatment instrument. Desirably, the submucosa of the disease portion P is exfoliated, using the same third treatment instrument. Thereafter, a hemostatic treatment is performed for the exfoliated portion, using high-frequency energy or the like, and the third treatment instrument is replaced with a fourth treatment instrument (e.g., grasping forceps) to recover the disease portion P.

When marking the periphery of the disease portion P, the operator holds the outer circumferential surface of the insertion section 22 of the endoscope 12 with the right hand, and pinches and holds the retainer body 152 of the second retainer 108 with the right hand. The distal surface 32a of the distal structural portion 32 of the insertion section 22 of the endoscope 12 is arranged to face the periphery of the disease portion P. In this state, the retainer body 152 of the second retainer 108 is advanced to project the insertion body 82 of the first treatment instrument 14 in the axial direction thereof. The portion with which the distal end of the end effector 94a is brought into contact is cauterized (marked). Then, the retainer body 152 of the second retainer 108 is retreated to retreat or pull the distal end of the insertion body 82 of the first treatment instrument 14 in the axial direction thereof toward the distal surface 32a of the insertion section 22 of the endoscope 12.

Then, the operator slightly moves the distal surface 32a of the insertion section 22 from the marking position along the periphery of the disease portion P. The distal surface 32a of the distal structural portion 32 of the insertion section 22 of the endoscope 12 is made to face the periphery of the disease portion P. In this state, the retainer body 152 of the second retainer 108 is moved to mark the periphery of the disease portion P by use of the distal end of the end effector 94a.

After the insertion section 22 of the endoscope 12 is moved, the retainer body 152 of the second retainer 108 is repeatedly advanced or retreated to mark the periphery of the disease portion P. During this procedure, the operator twists the insertion section 22 from the state shown in FIG. 1 to the state shown in FIG. 4, as needed. At the time, the operator bends the bendable section 34 by an operation with the left hand. In this manner, the operator can move the distal structural portion 32 along the periphery of the disease portion P, with the distal surface 32a facing the periphery of the disease portion P.

When the operator rotates the insertion section 22 around the axis thereof with the right hand, the right hand does not separate from the insertion section 22 or from the retainer body 152 of the second retainer 108. The operator does not lose sight of the disease portion P when the periphery of the disease portion P is marked.

Likewise, during the dissection of the disease portion P along the mark and during the exfoliation, the insertion section 22 and the retainer body 152 of the second retainer 108 are kept held with the right hand. In addition, the dissection depth and the dissection direction can be adjusted by properly moving the retainer body 152 of the second retainer 108. For example, the operator can adjust the dissection depth by advancing or retreating the retainer body 152 in the axial direction of the insertion body 82. The dissection direction can be adjusted by rotating the retainer body 152 around the axis of the insertion body 82, though this feature is dependent on the shape of the end effector 94a of the treatment instrument 14.

When the disease portion P is dissected and exfoliated using high-frequency energy, the operator signals the assistant that the energy is to be output.

As described above, in the ESD treatment, the operator properly moves the distal surface 32a of the distal structural portion 32 of the insertion section 22 of the endoscope 12 to a desirable position and mares the distal surface 32a face the periphery of the disease portion P. In this state, the operator can properly move the distal end of the insertion body 82 of the treatment instrument 14, while holding the retainer body 152.

During the treatment, the treatment instrument valve 136 having a valve structure prevents blood or the like from leaking from the treatment instrument valve 136 to the outside of the assist device main body 16a. When the treatment instrument 14 is replaced with another and when the treatment ends, the assistant pulls the insertion body 82 of the treatment instrument 14 out of the channel 40 and the passage 120 of the assist device main body 16a. At such times as well, the treatment instrument valve 136 having a valve structure prevents blood or the like from leaking.

The assist device 16 is washed, disinfected and sterilized for reuse. If the retainer body 152 of the second retainer 108 is degraded after repeated use and should be replace with a new one, the second retainer 108 is detached from the first retainer 106. When the second retainer 108 is replaced with a new one, the connecting member 110 may also be replaced with a new one. Alternatively, the same connecting member 110 may be used in combination with the new second retainer. Where the new connecting member 110 is used, the new second retainer 108 is supported by the first retainer 106 by means of the new connecting member 110.

As described above, the endoscope system 10 of the present embodiment, particularly the assist device 16, has the following features:

The second retainer 108 is fitted around the thin insertion body 82 of the treatment instrument 14 in a direction different from the longitudinal direction of the insertion body 82. Even though the insertion body 82 of the treatment instrument 14 is thin, it can be advanced or retreated (pushed or pulled), without slipping, in the axial direction thereof together with the second retainer 108. In addition, it can be rotated around the axis thereof. The operator can therefore complete the treatment efficiently and in a short time. Accordingly, the use of the assist device 16 having the second retainer 108 reduces the burden on the operator, and further reduces the burden on the patient as well.

Of the portions of the second retainer 108, that portion which is held by the operation has an outer diameter larger than the outer diameter of the insertion body 82 of the treatment instrument 14. With this structure, the second retainer 108 is easier to pinch than the insertion body 82 of the treatment instrument 14. In particular, fine adjustment of the rotation of the insertion body 82 is easy to make. Accordingly, the operator can easily direct the end effector 94a of the treatment instrument 14 in any direction desired.

Although the second retainer (treatment retaining member) 108 is used, it can be said that the insertion body 82 of the treatment instrument 14 is directly pinched and operated. With this structure, the operator can feel how the end effector 94a at the end of the insertion body 82 of the treatment instrument 14 works and perform treatment of the disease portion P based on the feeling.

The first retainer 106 can be attached to the outer circumferential surface of the insertion section 22 immediately before the start of the treatment, and the second retainer 108 can be easily attached to the insertion body 82 of the treatment instrument 14. Unlike the assist device disclosed in International Publication No. 2013/065509, the insertion body does not have to be passed through a narrow holding structure. When the treatment of the disease portion P is started in the state where the distal surface 32a of the distal structural portion 32 of the insertion section 22 of the endoscope 12 faces the disease portion P, the first retainer 106 and the second retainer 108 can be moved to their optimal positions.

Since the second retainer 108 is movable relative to the first retainer 106, it can be arranged at a position where it is easy to operate, even if the insertion section 22 of the endoscope 12 is twisted. With this structure, the insertion body 82 of the treatment instrument 14 can be properly advanced, retreated or rotated relative to the channel 40 of the endoscope 12.

For example, in the assist device described in International Publication No. 2013/065509, the operation member for advancing or retreating a treatment instrument rotates together with the insertion section of the endoscope. In the assist device of International Publication No. 2013/065509, if the insertion section is twisted 180°, the operation member is also rotated 180°, in which state it cannot be easily operated. In contrast, the assist device 16 of the present embodiment is featured in that the second retainer 108 is movable. Even if the insertion section 22 is twisted, the second retainer 108 can be easily moved to any position desired, ensuring an easy operation.

As described above, even if the insertion section 22 of the endoscope 12 is twisted, the operator does not have to separate the right hand from the insertion section 22 and yet can advance, retreat or rotate the insertion body 82 of the treatment instrument 14 relative to the channel 40 of the endoscope 12, using the thumb and the index finger of the right hand. As a result, a high-level ESD treatment, in which the insertion body 82 of the treatment instrument 14 has to be moved delicately, can be performed accurately, safely and in a short time.

Accordingly, the assist device 16 of the present embodiment is an assist device that enables a treatment instrument 14 to be moved inside the channel 40 of the endoscope 12, without the operability of the treatment instrument 14 being degraded by the twisted condition of the insertion section 22 of the endoscope 12, namely, the movement performance, including the advancing/retreating performance and the rotation performance, being degraded. An endoscope system 10 including such an assist device 16 can be provided.

When the right hand is separated from the insertion section 22, the twisted amount decreases due to the weight of the insertion section 22 and the reaction to the twisting operation. As a result, the distal end of the insertion section 22 inevitably moves. In particular, where the distal end portion of the insertion section 22 is largely twisted, the repulsive force of the insertion section 22 is large, and the returning quantity is large. For this reason, once the operator's right hand loses hold of the insertion section 22, the operator has to hold the insertion section 22 again and properly operate it while confirming the observation image captured by the observation optical system. Specifically, the operator has to return to the state in which a front view of the disease portion P is observed, and resume the dissection operation using the treatment instrument. Because of the use of the assist device 16 of the present embodiment, the operator continues to hold the insertion section 22 with the right hand from the start of the treatment (when the assist device 16 is attached to the endoscope 12, with the distal surface 32a being made to face the disease portion P) to the end of the treatment (when the disease portion P is caught and held with a treatment instrument 14 such as grasping forceps).

Since the second retainer 108 has a simple structure, the assist device 16 can be washed and sterilized in a short time after the treatment. Even if the second retainer 108 deteriorates, only the second retainer 108 can be replaced with a new one. Accordingly, the cost of the assist device 16 can be low.

Figure 3B:
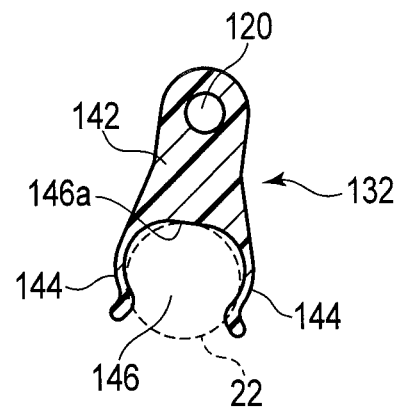
FIG. 3B is a sectional view taken along line 3B-3B shown in FIG. 3A.
Figure 3C:
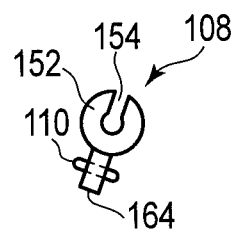
FIG. 3C is a schematic diagram illustrating how a second retainer of the accessory shown in FIG. 3A looks like when it is viewed in the direction indicated by arrow 3C.
Figure 5A:
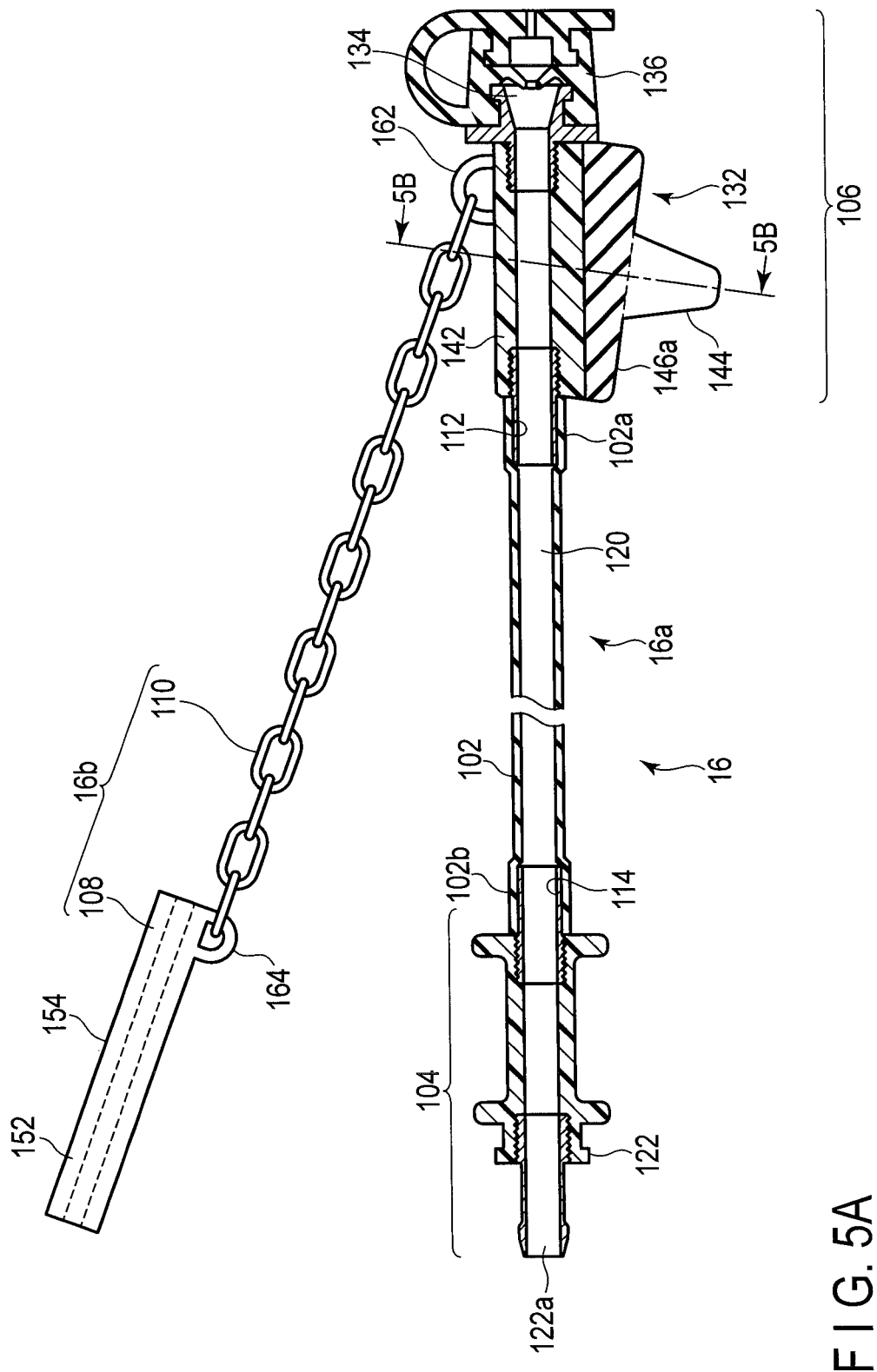
FIG. 5A shows the assist device of an endoscope system according to a modification of the first embodiment, the main body of the assist device being depicted as a longitudinal sectional view, and an accessory depicted as a schematic diagram.

With reference to FIGS. 3A and 3B, a description was given of the case where the base 142 of the main body 132 of the first retainer 106 of the assist device main body 16a and the paired arms 144 are integrally formed of a plastic resin material. As shown in FIGS. 5A and 5B, the base 142 of the main body 132 of the first retainer 106 of the assist device main body 16a may be formed of a plastic resin material, and the paired arms 144 and the contact surface 146a may be integrally formed of a rubber material. This structure is preferred as well.

FIGS. 6A and 6B show a modification of the accessory 16b of the assist device 16. The second retainer 108 of this modification has a shape different from that shown in FIGS. 3A and 3C. In this modification, the retainer body 152a is a clip member made of a single elastically-deformable plate. The retainer body 152a is formed by bending a substantially rectangular plate member until the end portions 154a of the same surface are in contact with each other or close to each other. The end portions 154a are used in the same way as the slit 154 described above. The end portions 154a of the retainer body 152a, which are in contact with each other or close to each other, are elastically deformed, and the retainer body 152a of the modification functions in a similar manner to the retainer body 152 shown in FIGS. 3A and 3C.

The retainer body 152a is not limited to any specific material, as long as the retainer body 152a enables the insertion body 82 of the treatment instrument 14 to be easily held without slipping in a direction different from the axial direction of the insertion body 82 of the treatment instrument, for example, in a direction perpendicular to the axial direction of the insertion body 82.

Likewise, the retainer body of the second retainer 108 is not limited to any specific material or shape, as long as the retainer body enables the insertion body 82 of the treatment instrument 14 to be easily held without slipping in a direction perpendicular to the axial direction of the insertion body 82 of the treatment instrument 14.

A second embodiment will be described with reference to FIG. 7. The second embodiment is a modification of the first embodiment, including all modifications mentioned above. Elements which are similar to those described in connection with the first embodiment or which have similar functions to those described in connection with the first embodiment will be denoted by the same reference symbols, and a detailed description of such elements will be omitted.

The endoscope system 210 of the second embodiment includes an endoscope 212, a treatment instrument 214 and the assist device 16.

Reference will be made to the case where the endoscope 212 is not a front viewing endoscope 12 described in connection with the first embodiment but a side viewing endoscope 212. The side viewing, endoscope 212 of this embodiment is applied to treatment of a duodenum, for example.

An insertion section 22 includes a distal structural portion 232 incorporating a treatment instrument elevator 232a, a bendable section 34 and a flexible tube 36. As is known in the art, the distal structural portion 232 is configured such that the distal end of a channel 40 is located on the distal side of the treatment instrument elevator 232a. The distal structural portion 232 is provided with an observation window and an illumination window which are juxtaposed to the treatment instrument elevator 232a though these windows are not illustrated.

Like a known type of side viewing endoscope, an operation section main body 68 is provided with a treatment instrument elevator operation lever 278 used for adjusting the raised state of the treatment instrument elevator 232a. The treatment instrument elevator operation lever 278 is operated with the thumb of the left hand of the operator.

A treatment instrument 214 used in this embodiment includes a radiopaque tube 282 (which is an insertion body) and a base 284. The base 284 contains a contrast medium which is to be injected into a pancreatic duct PD and a bile duct BD by way of the radiopaque tube 282.

Figure 7:
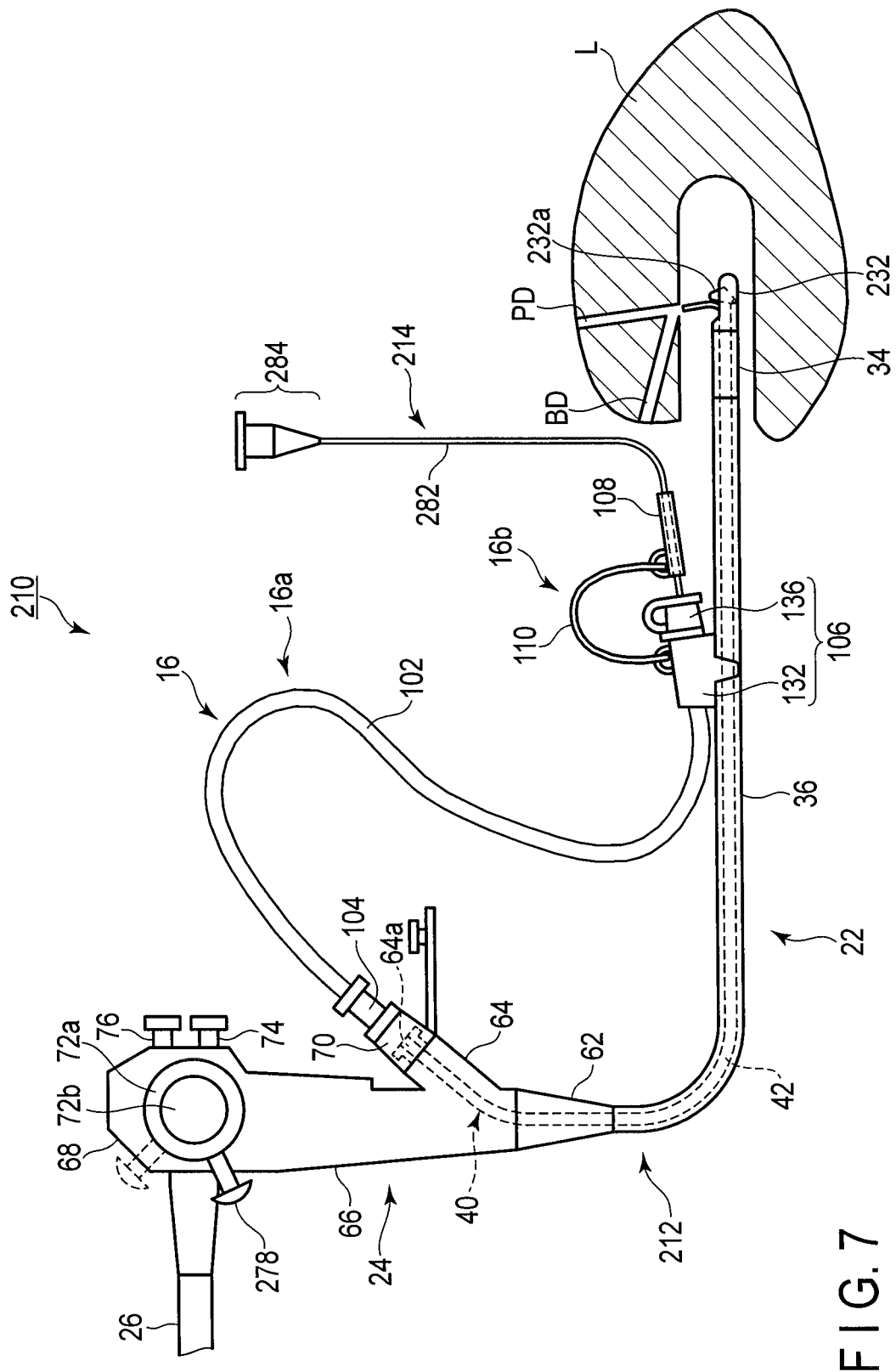
FIG. 7 is a schematic diagram showing an endoscope system according to the second embodiment and illustrating a state where a treatment instrument is inserted into an assist device or the channel of an endoscope, with the assist device attached to the endoscope.

FIG. 7 illustrates that an endoscopic retrograde cholangiopancreatography (ERCP) is performed, in which the radiopaque tube 282 is inserted into the bile duct through the duodenal papilla, a contrast medium is injected into the bile duct, and an X-ray image of a disease portion is taken.

First, the operator inserts the distal structural portion 32 of the insertion section 22 of the endoscope 12 into the duodenum by way of the oral cavity, the esophagus and the stomach. The radiopaque tube 282 filled with the contrast medium is inserted through the passage 120 of the assist device main body 16a and the channel 40 of the endoscope 212, and the distal end of the radiopaque tube 282 (insertion body) is projected from the distal end of the distal structural portion 32. The treatment instrument elevator operation lever 278 is operated to properly raise the treatment instrument elevator 232a, and the distal end of the radiopaque tube 282 is opposed to the duodenal papilla. In the state where the insertion section 22 is held with the right hand of the operator, the second retainer 108 of the assist device 16 is advanced or retreated to move the radiopaque tube 282, and the distal end of the radiopaque tube 282 is pushed into the duodenal papilla.

With the insertion section 22 held with the right hand, the second retainer 108 attached to the radiopaque tube 282 is pinched with the thumb and the index finger of the right hand, and the radiopaque tube 282 is advanced (pushed), retreated (pulled) and rotated around the axis, as needed. As can be seen, the operation (push, pull and twist) of the insertion section 22 and the operation (push, pull and rotation) of the radiopaque tube 282 can be performed simultaneously. Accordingly, the radiopaque tube 282 can be easily inserted into the pancreatic duct PD and bile duct BD, which extend in a complicated fashion.

A contrast medium is injected into the pancreatic duct PD and the bile duct BD from the radiopaque tube 282.

As described above, the assist device 16 can be used not only for the front viewing endoscope 12 but also for the side viewing endoscope 212, and the distal end of the radiopaque tube 282 of the treatment instrument 214 can be moved to a proper position relative to the distal end of the insertion section 22.

Additional advantages and modifications will readily occur to those skilled in the art. Therefore, the invention. in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An assist device which is applied to a treatment instrument, the treatment instrument including an insertion body to be inserted through a channel of an insertion section of an endoscope, the assist device being configured to assist movement of the insertion body relative to the channel, the assist device comprising:
   a flexible tube including a passage into which the insertion body of the treatment instrument is inserted, the flexible tube including one end and an other end;
   a connector configured to connect the one end of the flexible tube to the channel such that the passage communicates with the channel;
   a first retainer configured to attach a side of the other end of the flexible tube to an outer circumference of the insertion section of the endoscope or to an outer circumference of an operation section connected to the insertion section;
   a second retainer being movable relative to the first retainer and configured to hold the insertion body of the treatment instrument; and
   a connecting member connecting the first retainer and the second retainer to each other,
   wherein the second retainer is detachably attached to the insertion body of the treatment instrument in a direction different from a longitudinal direction of the insertion body.

2. The assist device according to claim 1, wherein the first retainer is attachable to and detachable from the insertion section of the endoscope.

3. The assist device according to claim 1, wherein the second retainer includes an elastic member.

4. The assist device according to claim 1, wherein the second retainer is attachable to and detachable from the connecting member, or the connecting member is attachable to and detachable from the first retainer, together with the second retainer.

5. The assist device according to claim 1, wherein the first retainer is attached near an end of the flexible tube.

6. An endoscope system comprising:
an endoscope including a channel;
an assist device as defined in claim 1 and connected to an end of the channel by the connector; and
a treatment instrument including an insertion body which is configured to insert into the passage of the assist device and the channel of the insertion section of the endoscope and which is held by the second retainer.

7. The endoscope system according to claim 6, wherein the second retainer is movable closer to or away from the first retainer.

8. The assist device according to claim 1, wherein the connecting member includes a proximal end and a distal end, and
the second retainer is movable relative to the first retainer within a range defined by a length between the proximal end and the distal end of the connecting member.

9. The assist device according to claim 1, wherein the second retainer comprises:
an elastically-deformable tubular retainer body; and
a slit which extends throughout the overall length from one end to an other of the retainer body along a longitudinal axis of the retainer body; and
the slit is configured to allow communication between an inside and an outside of the retainer body.

10. The assist device according to claim 1, wherein the connecting member comprises one of a chain, a cord member, a flexible member, a stretchable member, or a vinyl tie.

11. The assist device according to claim 1, wherein:
the second retainer includes a slit through which the insertion body is passed, the second retainer retaining the insertion body through the slit; and
the slit has a width substantially equal to an outer diameter of the insertion body or slightly less than the outer diameter of the insertion body.

12. The assist device according to claim 1, wherein the connecting member is configured to move the second retainer to a position where the second retainer is configured to be held with respect to the first retainer, without reference to whether or not the insertion section is twisted or how the insertion section is twisted.

* * * * *